US006759527B2

(12) United States Patent
Yu et al.

(10) Patent No.: US 6,759,527 B2
(45) Date of Patent: Jul. 6, 2004

(54) HUMAN KINASE AND POLYNUCLEOTIDES ENCODING THE SAME

(75) Inventors: Xuanchuan Yu, Conroe, TX (US); Maricar Miranda, Houston, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 201 days.

(21) Appl. No.: 10/103,547

(22) Filed: Mar. 20, 2002

(65) Prior Publication Data

US 2003/0166888 A1 Sep. 4, 2003

Related U.S. Application Data

(60) Provisional application No. 60/277,168, filed on Mar. 20, 2001, now abandoned.

(51) Int. Cl.[7] .................. C07H 21/04; C07H 21/02; C12N 9/12; C12N 1/20; C12N 15/00
(52) U.S. Cl. .................. 536/23.2; 435/194; 435/320.1; 435/6; 435/252.3; 536/23.1
(58) Field of Search ............................. 536/23.2, 23.1; 435/194, 320.1, 252.3, 6

(56) References Cited

U.S. PATENT DOCUMENTS

| | | | |
|---|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,873,191 A | 10/1989 | Wagner et al. |
| 4,946,778 A | 8/1990 | Ladner et al. |
| 5,252,743 A | 10/1993 | Barrett et al. |
| 5,272,057 A | 12/1993 | Smulson et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,700,637 A | 12/1997 | Southern |
| 5,723,323 A | 3/1998 | Kauffman et al. |
| 5,744,305 A | 4/1998 | Fodor et al. |
| 5,817,479 A | 10/1998 | Au-Young et al. |
| 5,830,721 A | 11/1998 | Stemmer et al. |
| 5,837,458 A | 11/1998 | Minshull et al. |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,117,679 A | 9/2000 | Stemmer |
| 6,150,584 A | 11/2000 | Kucherlapati et al. |

OTHER PUBLICATIONS

Inagaki et al., BBRC, 265, 462–468, 1999.*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1961, "A New Dominant Hybrid Selective Marker for Higher Eukaryotic Cells", J. Mol. Biol, 150:1–14.
Gautier et al, 1987, "α–DNA IV:α–anomeric and β–anomeric tetrathymidylates covalently inked to Intercalating oxazolopyridocarbazole. Synthesis, physiochemical properities and Poly (rA) binding", Nucleic Acids Research 15(16):6625–6641.
Gordon, 1989, "Transgenic Animals", International Review of Cytology, 115:171–229.
Greenspan et al, 1993, "Idiotypes: Structure and immunogenicity", FASEB Journal 7:437–444.
Gu et al, 1994, "Deletion of a DNA Polymerase β Gene Segment in T Cells Using Cell Type–Specific Gene Targeting", Science 265:103–106.
Huse et al, 1989, "Generation of a Large Combinatorial Library of the Immunoglobulin Repertoire in Phage Lambda", Science 246:1275–1281.
Huston et al, 1988, "Protein engineering of antibody binding sites: Recovery of specific activity in an anti–digoxin single–chain FV analogue produced In Escherichia ooll", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985,"Up–promoter mutations in the Ipp gene of Escherichia coli", Nucleic Acids Research 13(9):3101–3110.
Janknecht et al,1991, "Rapid and efficient purification of native histidine–tagged protein expressed by recombinant vaccinla virus", PNAS 88:8972–8976.
Kohlar & Milstein,1975,"Continuous cultures of fused cells secreting antibody at predefined specificity", Nature 256:495–497.
Lakso et al, 1992, "Targeted oncogene activation by site–specific recombination in transgenic mice", Proc. Natl. Acad. Sci. USA 89:6232–6236.
Lavitrano et al, 1989, "Sperm Cells as Vectors for Introducing Foreign DNA into Eggs: Genetic Transformation of Mice", Cells 57:717–723.
Lo, 1983, "Transformation by Iontophoretic Microinjection of DNA: Multiple Integrations without Tandem Insertions", Mol. & Cell. Biology 3(10) :1803–1814.
Logan et al, 1964, "Adenovirus tripartite leader sequence enhances translation of mRNAs late after infection", Proc. Natl. Acad. Sci. USA 81:3655–3659.
Lowy et al, 1980, "Isolation of Transfroming DNA: Cloning the Hamster aprt Gene", Cell 22:817–823.

(List continued on next page.)

Primary Examiner—Maryam Monshipouri

(57) ABSTRACT

Novel human polynucleotide and polypeptide sequences are disclosed that can be used in therapeutic, diagnostic, and pharmacogenomic applications.

3 Claims, No Drawings

OTHER PUBLICATIONS

Morrison et al, 1984, "Chimeric human antibody molecules: Mouse antigen–binding domains with human constant region domains", Proc. Natl. Acad. Sci. USA 81:6851–6855.

Mulligan & Berg, 1961,"Selection for animal cells that express the Escherichia coli gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy Identification of cDNA clones", EMBO Journal 2(10):1791–1794.

Santerre et al, 1984, "Expression of prokaryotic genes for hygromycin B and G41B resistance as dominant–slelction markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983,"Molecular Engineering of the Autographa californica Nuclear Polyhedrosis Virus Genome: Deletion Mutations within the Polyhedrin Gene", J. Virol. 46(2):584–593.

Stein et al, 1988, "Physiochemical properties of phosphorothloate oligodeoxynucleotides", Nucleic Acids Research 16(8)3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takada et al, 1985, "Construction of chimaeric processed immunoglobulin genes containing mouse variable and human constant region sequences", Nature 314:452–451.

Thompson et al, 1989, "Germ Line Transmission and Expression of a Corrected HPRT Gene Produced by Gane Targeting in Embryonic Stem Cells", Cell 56:313–321.

Van Der Putten et al, 1985, "Efficient insertion of genes into the mouse germ line via retroviral vectors", Proc. Natl. Acad. Sci. USA 82:6148–6152.

Van Heeke et al, 1989, "Expression of Human Asparagine Synthetase in Escherichia coli", J. Biol. Chemistry 264(10):5503–5509.

Ward et al, 1989, "Binding activities of a repertoire of single immunoglobulin variable domains secreted from Escherichia coli", Nature 341:544–546.

Wigler et al, 1977, "Transfer of Purified Herpes Virus Thymidine Kinase Gene to Cultured Mouse Cells", Cell 11:223–232.

Wigler et al, 1980, "Transformation of mammallan cells with an amplifiable dominant–acting gene", Proc. Natl. Acad. Sci. USA 77(6):3567–3570.

* cited by examiner

SEQUENCE LISTING

<160> NUMBER OF SEQ ID NOS: 2

<210> SEQ ID NO 1
<211> LENGTH: 1368
<212> TYPE: DNA
<213> ORGANISM: Homo sapiens

<400> SEQUENCE: 1

```
atgaggattg tttgtttagt gaaaaaccaa cagcccctgg gagccaccat caagcgccac      60
gagatgacag gggacatctt ggtggccagg atcatccacg gtgggctggc ggagagaagt     120
gggttgctat atgctggaga caaactggta gaagtgaatg gagtttcagt tgagggactg     180
gaccctgaac aagtgatcca tattctggcc atgtctcgag gcacaatcat gttcaaggtg     240
gttccagtct ctgaccctcc tgtgaatagc cagcagatgg tgtacgtccg tgccatgact     300
gagtactggc cccaggagga tcccgacatc ccctgcatgg acgctggatt gcctttccag     360
aagggggaca tcctccagat tgtggaccag aatgatgccc tctggtggca ggcccgaaaa     420
atctcagacc ctgctacctg cgctgggctt gtcccttcta accaccttct gaagaggaag     480
caacgggaat tctggtggtc tcagccgtac cagcctcaca cctgcctcaa gtcaaccct a    540 tacaaggagg agtttgttgg ctacggtcag aagttcttta tagctggctt ccgccgcagc     600
atgcgccttt gtcgcaggaa gtctcacctc agcccgctgc atgccagtgt gtgctgcacc     660
ggcagctgct acagtgcagt gggtgcccct tacgaggagg tggtgaggta ccagcgacgc     720
ccttcagaca agtaccgcct catagtgctc atgggaccct ctggtgttgg agtaaatgag     780
ctcagaagac aacttattga atttaatccc agccattttc aaagtgctgt gccacacact     840
actcgtacta aaaagagtta cgaaatgaat gggcgtgagt atcactatgt gtccaaggaa     900
acatttgaaa acctcatata tagtcacagg atgctggagt atggtgagta caaaggccac     960
ctgtatggca ctagtgtgga tgctgttcaa acagtccttg tcgaaggaaa gatctgtgtc    1020
atggacctag agcctcagga tattcaaggg gttcgaaccc atgaactgaa gccctatgtc    1080
atatttataa agccatcgaa tatgaggtgt atgaaacaat ctcggaaaaa tgccaaggtt    1140
attactgact actatgtgga catgaagttc aaggatgaag acctacaaga gatggaaaat    1200
ttagcccaaa gaatggaaac tcagtttggc caattttttg atcatgtgat tgtgaatgac    1260
agcttgcacg atgcatgtgc ccagttgttg tctgccatac agaaggctca ggaggagcct    1320
```
cagtgggtac cagcaacatg gatttcctca gatactgagt ctcaatga        1368

<210> SEQ ID NO 2
<211> LENGTH: 455
<212> TYPE: PRT
<213> ORGANISM: Homo sapiens

<400> SEQUENCE: 2

Met Arg Ile Val Cys Leu Val Lys Asn Gln Gln Pro Leu Gly Ala Thr
1               5                   10                  15

Ile Lys Arg His Glu Met Thr Gly Asp Ile Leu Val Ala Arg Ile Ile
            20                  25                  30

His Gly Gly Leu Ala Glu Arg Ser Gly Leu Leu Tyr Ala Gly Asp Lys
        35                  40                  45

Leu Val Glu Val Asn Gly Val Ser Val Glu Gly Leu Asp Pro Glu Gln
    50                  55                  60

Val Ile His Ile Leu Ala Met Ser Arg Gly Thr Ile Met Phe Lys Val
65                  70                  75                  80

Val Pro Val Ser Asp Pro Pro Val Asn Ser Gln Gln Met Val Tyr Val
                85                  90                  95

Arg Ala Met Thr Glu Tyr Trp Pro Gln Glu Asp Pro Asp Ile Pro Cys
            100                 105                 110

Met Asp Ala Gly Leu Pro Phe Gln Lys Gly Asp Ile Leu Gln Ile Val
        115                 120                 125

Asp Gln Asn Asp Ala Leu Trp Trp Gln Ala Arg Lys Ile Ser Asp Pro
    130                 135                 140

Ala Thr Cys Ala Gly Leu Val Pro Ser Asn His Leu Leu Lys Arg Lys
145                 150                 155                 160

Gln Arg Glu Phe Trp Trp Ser Gln Pro Tyr Gln Pro His Thr Cys Leu
                165                 170                 175

Lys Ser Thr Leu Tyr Lys Glu Glu Phe Val Gly Tyr Gly Gln Lys Phe
            180                 185                 190

Phe Ile Ala Gly Phe Arg Arg Ser Met Arg Leu Cys Arg Arg Lys Ser
        195                 200                 205

His Leu Ser Pro Leu His Ala Ser Val Cys Cys Thr Gly Ser Cys Tyr
    210                 215                 220

Ser Ala Val Gly Ala Pro Tyr Glu Glu Val Val Arg Tyr Gln Arg Arg
225                 230                 235                 240

Pro Ser Asp Lys Tyr Arg Leu Ile Val Leu Met Gly Pro Ser Gly Val
                245                 250                 255

Gly Val Asn Glu Leu Arg Arg Gln Leu Ile Glu Phe Asn Pro Ser His
            260                 265                 270

Phe Gln Ser Ala Val Pro His Thr Thr Arg Thr Lys Lys Ser Tyr Glu
        275                 280                 285

Met Asn Gly Arg Glu Tyr His Tyr Val Ser Lys Glu Thr Phe Glu Asn
    290                 295                 300

Leu Ile Tyr Ser His Arg Met Leu Glu Tyr Gly Glu Tyr Lys Gly His
305                 310                 315                 320

Leu Tyr Gly Thr Ser Val Asp Ala Val Gln Thr Val Leu Val Glu Gly
                325                 330                 335

Lys Ile Cys Val Met Asp Leu Glu Pro Gln Asp Ile Gln Gly Val Arg
            340                 345                 350

Thr His Glu Leu Lys Pro Tyr Val Ile Phe Ile Lys Pro Ser Asn Met
        355                 360                 365

―continued

```
Arg Cys Met Lys Gln Ser Arg Lys Asn Ala Lys Val Ile Thr Asp Tyr
    370                 375                 380

Tyr Val Asp Met Lys Phe Lys Asp Glu Asp Leu Gln Glu Met Glu Asn
385                 390                 395                 400

Leu Ala Gln Arg Met Glu Thr Gln Phe Gly Gln Phe Phe Asp His Val
                405                 410                 415

Ile Val Asn Asp Ser Leu His Asp Ala Cys Ala Gln Leu Leu Ser Ala
                420                 425                 430

Ile Gln Lys Ala Gln Glu Glu Pro Gln Trp Val Pro Ala Thr Trp Ile
        435                 440                 445

Ser Ser Asp Thr Glu Ser Gln
    450                 455
```

HUMAN KINASE AND POLYNUCLEOTIDES ENCODING THE SAME

The present application claims the benefit of U.S. Provisional Application No. 60/277,168 which was filed on Mar. 20, 2001 now abandond, and is herein incorporated by reference in its entirety.

INTRODUCTION

The present invention relates to the discovery, identification, and characterization of novel human polynucleotides encoding a kinase which share sequence similarity with animal kinases. The invention encompasses the described polynucleotides, host cell expression systems, the encoded proteins, fusion proteins, polypeptides and peptides, antibodies to the encoded proteins and peptides, and genetically engineered animals that either lack or over-express the disclosed genes, antagonists and agonists of the proteins, and other compounds that modulate the expression or activity of the proteins encoded by the disclosed genes, which can be used for diagnosis, drug screening, clinical trial monitoring, the treatment of diseases and disorders, and cosmetic or nutriceutical applications.

BACKGROUND OF THE INVENTION

Kinases mediate the phosphorylation of a wide variety of proteins and compounds in the cell. In conjunction with phosphatases, kinases are involved in a range of regulatory pathways. Given the physiological importance of kinases, they have been subject to intense scrutiny and are proven drug targets.

SUMMARY OF THE INVENTION

The present invention relates to the discovery, identification, and characterization of nucleotides that encode novel a human kinase and the corresponding amino acid sequence of this protein. The novel human kinases (NHK) described for the first time herein shares structural similarity with animal kinases, including, but not limited to, receptor tyrosine kinases and especially kinases of the membrane-associated guanylate kinase (MAGUK) family. The described NHK encoding sequences define a novel kinase having homologues and orthologs across a range of phyla and species.

The novel human polynucleotide described herein, encode an open reading frame (ORF) of 455 amino acids in length (see SEQ ID NO: 2).

The invention also encompasses agonists and antagonists of the described NHK, including small molecules, large molecules, mutant NHKs, or portions thereof, that compete with native NHK, peptides, and antibodies, as well as nucleotide sequences that can be used to inhibit the expression of the described NHK (e.g., antisense and ribozyme molecules, and open reading frame or regulatory sequence replacement constructs) or to enhance the expression of the described NHK (e.g., expression constructs that place the described polynucleotide under the control of a strong promoter system), and transgenic animals that express a NHK sequence, or "knock-outs" (which can be conditional) that do not express a functional NHK. Such knock-out mice can be produced in several ways, one of which involves the use of mouse embryonic stem cell ("ES cells") lines that contain gene trap mutations in a murine homolog of the described NHK. When the unique NHK sequences described in SEQ ID NOS:1–2 are "knocked-out" they provide a method of identifying phenotypic expression of the particular gene as well as a method of assigning function to previously unknown genes. In addition, animals in which the unique NHK sequences described in SEQ ID NOS:1–2 are "knocked-out" provide a unique source in which to elicit antibodies to homologous and orthologous proteins which would have been previously viewed by the immune system as "self" and therefore would have failed to elicit significant antibody responses.

Additionally, the unique NHK sequences described in SEQ ID NOS:1–2 are useful for the identification of protein coding sequence and mapping a unique gene to a particular chromosome. These sequences identify actual, biologically verified, and therefore relevant, exon splice junctions as opposed to those that may have been bioinformatically predicted from genomic sequence alone. The sequences of the present invention are also useful as additional DNA markers for restriction fragment length polymorphism (RFLP) analysis, and in forensic biology.

Further, the present invention also relates to processes for identifying compounds that modulate, i.e., act as agonists or antagonists, of NHK expression and/or NHK activity that utilize purified preparations of the described NHK and/or NHK products, or cells expressing the same. Such compounds can be used as therapeutic agents for the treatment of any of a wide variety of symptoms associated with biological disorders or imbalances.

DESCRIPTION OF THE SEQUENCE LISTING AND FIGURES

The Sequence Listing provides the sequence of the novel human ORF encoding the described novel human kinase protein.

DETAILED DESCRIPTION OF THE INVENTION

The NHK described for the first time herein defines a novel protein that is expressed in, inter alia, human cell lines and fetal brain, spinal cord, lymph node, bone marrow, adrenal gland, fetal kidney, and fetal lung cells.

The present invention encompasses the nucleotides presented in the Sequence Listing, host cells expressing such nucleotides, the expression products of such nucleotides, and: (a) nucleotides that encode mammalian homologs of the described genes, including the specifically described NHK, and related NHK products; (b) nucleotides that encode one or more portions of a NHK that correspond to functional domains, and the polypeptide products specified by such nucleotide sequences including, but not limited to, the novel regions of any active domain(s); (c) isolated nucleotides that encode mutant versions, engineered or naturally occurring, of the described NHK in which all or a part of at least one domain is deleted or altered, and the polypeptide products specified by such nucleotide sequences including, but not limited to, soluble proteins and peptides in which all or a portion of the signal sequence is deleted; (d) nucleotides that encode chimeric fusion proteins containing all or a portion of a coding region of a NHK, or one of its domains (e.g., a receptor/ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing. As discussed above, the present invention includes: (a) the human DNA sequences presented in the Sequence Listing (and vectors comprising the same) and additionally contemplates any nucleotide sequence encoding a contiguous NHK open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/ 0.1% SDS at 68° C. ((Ausubel F. M. et al., eds., 1989, Current Protocols in Molecular Biology, Vol. I, Green Publishing Associates, Inc., and John Wiley & Sons, Inc., New York, at p. 2.10.3) and encodes a functionally equivalent expression product.

Additionally contemplated are any nucleotide sequences that hybridize to the complement of the DNA sequence that encode and express an amino acid sequence presented in the Sequence Listing under moderately stringent conditions, e.g., washing in 0.2×SSC/0.1% SDS at 42° C. (Ausubel et al., 1989, supra), yet still encode a functionally equivalent NHK product. Functional equivalents of a NHK include naturally occurring NHKs present in other species and mutant NHKs whether naturally occurring or engineered (by site directed mutagenesis, gene shuffling, directed evolution as described in, for example, U.S. Pat. Nos. 5,837,458 or 5,723,323 both of which are herein incorporated by reference). The invention also includes degenerate nucleic acid variants of the disclosed NHK polynucleotide sequences.

Additionally contemplated are polynucleotides encoding NHK ORFs, or their functional equivalents, encoded by polynucleotide sequences that are about 99, 95, 90, or about 85 percent similar to corresponding regions of a NHK (as measured by BLAST sequence comparison analysis using, for example, the GCG sequence analysis package using default parameters).

The invention also includes nucleic acid molecules, preferably DNA molecules, that hybridize to, and are therefore the complements of, the described NHK encoding polynucleotides. Such hybridization conditions can be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHK oligonucleotides can be used as hybridization probes for screening libraries, and assessing gene expression patterns (particularly using a micro array or high-throughput "chip" format). Additionally, a series of the described NHK oligonucleotide sequences, or the complements thereof, can be used to represent all or a portion of the described NHK sequences. An oligonucleotide or polynucleotide sequence first disclosed in at least a portion of SEQ ID NO: 1 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence which is first disclosed in at least a portion of SEQ ID NO: 1, or, where protein chips are contemplated, an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631, 211, 5,445,934, 5,252,743, 4,713,326, 5,424,186, and 4,689, 405 the disclosures of which are herein incorporated by reference in their entirety.

Addressable arrays comprising sequences first disclosed in at least a portion of SEQ ID NOS:1–2 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from a sequence first disclosed in at least a portion of SEQ ID NO:1.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in at least a portion of SEQ ID NO:1 provides detailed information about transcriptional changes involved in a specific pathway, potentially leading to the identification of novel components or gene functions that manifest themselves as novel phenotypes.

Probes consisting of sequences first disclosed in at least a portion of SEQ ID NO:1 can also be used in the identification, selection and validation of novel molecular targets for drug discovery. The use of these unique sequences permits the direct confirmation of drug targets and recognition of drug dependent changes in gene expression that are modulated through pathways distinct from the drug's intended target. These unique sequences therefore also have utility in defining and monitoring both drug action and toxicity.

As an example of utility, the sequences first disclosed in at least a portion of SEQ ID NOS:1–2 can be utilized in microarrays or other assay formats, to screen collections of genetic material from patients who have a particular medical condition. These investigations can also be carried out using the sequences first disclosed in at least a portion of SEQ ID NOS:1–2 in silico and by comparing previously collected genetic databases and the disclosed sequences using computer software known to those in the art.

Thus the sequences first disclosed in at least a portion of SEQ ID NOS:1–2 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in at least a portion of SEQ ID NO: 1. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHK gene antisense molecules, useful, for example, in NHK gene regulation and/or as antisense primers in amplification reactions of NHK gene nucleic acid sequences. With respect to NHK gene regulation, such techniques can be used to regulate biological functions. Further, such sequences can be used as part of ribozyme and/or triple helix sequences that are also useful for NHK gene regulation.

Inhibitory antisense or double stranded oligonucleotides can additionally comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including, but not limited to, arabinose, 2-fluoroarabinose, xylulose, and hexose.

In yet another embodiment, the antisense oligonucleotide will comprise at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHK.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well-known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Spring Harbor Press, NY; and Ausubel et al., 1989, Current Protocols in Molecular Biology, Green Publishing Associates and Wiley Interscience, NY.

Alternatively, suitably labeled NHK nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

In another example, the present sequences can be used in restriction fragment length polymorphism (RFLP) analysis to identify specific individuals. In this technique, an individual's genomic DNA is digested with one or more restriction enzymes, and probed on a Southern blot to yield unique bands for identification (as generally described in U.S. Pat. No. 5,272,057, incorporated herein by reference). In addition, the sequences of the present invention can be used to provide polynucleotide reagents, e.g., PCR primers, targeted to specific loci in the human genome, which can enhance the reliability of DNA-based forensic identifications by, for example, providing another "identification marker" (i.e., another DNA sequence that is unique to a particular individual). Actual base sequence information can be used for identification as an accurate alternative to patterns formed by restriction enzyme generated fragments.

Further, a NHK gene homolog can be isolated from nucleic acid from an organism of interest by performing PCR using two degenerate or "wobble" oligonucleotide primer pools designed on the basis of amino acid sequences within the NHK products disclosed herein. The template for the reaction may be total RNA, mRNA, and/or cDNA obtained by reverse transcription of mRNA prepared from, for example, human or non-human cell lines or tissue known or suspected to express an allele of the NHK encoding genomic locus/gene.

The PCR product can be subcloned and sequenced to ensure that the amplified sequences represent the sequence of the desired NHK gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHK gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHK sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHK allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well-known to those of skill in the art. By comparing the DNA sequence of the mutant NHK allele to that of a corresponding normal NHK allele, the mutation(s) responsible for the loss or alteration of function of the mutant NHK gene product can be ascertained.

Alternatively, a genomic library can be constructed using DNA obtained from an individual suspected of or known to carry a mutant NHK allele (e.g., a person manifesting a NHK-associated phenotype such as, for example, immune disorders, obesity, high blood pressure, etc.), or a cDNA library can be constructed using RNA from a tissue known, or suspected, to express a mutant NHK allele. A normal NHK gene, or any suitable fragment thereof, can then be labeled and used as a probe to identify the corresponding mutant NHK allele in such libraries. Clones containing mutant NHK sequences can then be purified and subjected to sequence analysis according to methods well-known to those skilled in the art.

Additionally, an expression library can be constructed utilizing cDNA synthesized from, for example, RNA isolated from a tissue known, or suspected, to express a mutant NHK allele in an individual suspected of or known to carry such a mutant allele. In this manner, gene products made by the putatively mutant tissue may be expressed and screened using standard antibody screening techniques in conjunction with antibodies raised against a normal NHK product, as described below. (For screening techniques, see, for example, Harlow, E. and Lane, eds., 1988, "Antibodies: A Laboratory Manual", Cold Spring Harbor Press, Cold Spring Harbor, N.Y.)

Additionally, screening can be accomplished by screening with labeled NHK fusion proteins, such as, for example, alkaline phosphatase-NHK or NHK-alkaline phosphatase fusion proteins. In cases where a NHK mutation results in an expression product with altered function (e.g., as a result of a missense or a frameshift mutation), polyclonal antibodies to NHK are likely to cross-react with a corresponding mutant NHK expression product. Library clones detected via their reaction with such labeled antibodies can be purified and subjected to sequence analysis according to methods well-known in the art.

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721, 5,837,458, 6,117,679, and 5,723,323 which are herein incorporated by reference in their entirety.

The invention also encompasses (a) DNA vectors that contain any of the foregoing NHK coding sequences and/or their complements (i.e., antisense); (b) DNA expression vectors that contain any of the foregoing NHK coding sequences operatively associated with a regulatory element that directs the expression of the coding sequences (for example, baculovirus as described in U.S. Pat. No. 5,869,336 herein incorporated by reference); (c) genetically engineered host cells that contain any of the foregoing NHK coding sequences operatively associated with a regulatory element that directs the expression of the coding sequences in the host cell; and (d) genetically engineered host cells that express an endogenous NHK sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include, but are not limited to, the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

Where, as in the present instance, some of the described NHK peptides or polypeptides are thought to be cytoplasmic or nuclear proteins (although processed forms or fragments can be secreted or membrane associated), expression systems can be engineered that produce soluble derivatives of a NHK (corresponding to a NHK extracellular and/or intracellular domains, or truncated polypeptides lacking one or more hydrophobic domains) and/or NHK fusion protein products (especially NHK-Ig fusion proteins, i.e., fusions of a NHK domain to an IgFc), NHK antibodies, and anti-idiotypic antibodies (including Fab fragments) that can be used in therapeutic applications. Preferably, the above expression systems are engineered to allow the desired peptide or polypeptide to be recovered from the culture media.

The present invention also encompasses antibodies and anti-idiotypic antibodies (including Fab fragments), antagonists and agonists of a NHK, as well as compounds or nucleotide constructs that inhibit expression of a NHK sequence (transcription factor inhibitors, antisense and ribozyme molecules, or open reading frame sequence or regulatory sequence replacement constructs), or promote the expression of a NHK (e.g., expression constructs in which NHK coding sequences are operatively associated with expression control elements such as promoters, promoter/enhancers, etc.).

The NHK or NHK peptides, NHK fusion proteins, NHK nucleotide sequences, antibodies, antagonists and agonists can be useful for the detection of mutant NHKs or inappropriately expressed forms of NHK for the diagnosis of disease. The NHK proteins or peptides, NHK fusion proteins, NHK nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of a NHK in the body. The use of engineered host cells and/or animals can offer an advantage in that such systems allow not only for the identification of compounds that bind to the endogenous receptor/ligand of a NHK, but can also identify compounds that trigger NHK-mediated activities or pathways.

Finally, the NHK products can be used as therapeutics. For example, soluble derivatives such as NHK peptides/domains corresponding to the NHK, NHK fusion protein products (especially NHK-Ig fusion proteins, i.e., fusions of a NHK, or a domain of a NHK, to an IgFc), NHK antibodies and anti-idiotypic antibodies (including Fab fragments), antagonists or agonists (including compounds that modulate or act on downstream targets in a NHK-mediated pathway) can be used to directly treat diseases or disorders. For instance, the administration of an effective amount of soluble NHK, or a NHK-IgFc fusion protein or an anti-idiotypic antibody (or its Fab) that mimics the NHK could activate or effectively antagonize the endogenous NHK or a protein interactive therewith. Nucleotide constructs encoding such NHK products can be used to genetically engineer host cells to express such products in vivo; these genetically engineered cells function as "bioreactors" in the body delivering a continuous supply of a NHK, a NHK peptide, or a NHK fusion protein to the body. Nucleotide constructs encoding functional NHKs, mutant NHKs, as well as antisense and ribozyme molecules can also be used in "gene therapy" approaches for the modulation of NHK expression. Thus, the invention also encompasses pharmaceutical formulations and methods for treating biological disorders.

Various aspects of the invention are described in greater detail in the subsections below.

THE NHK SEQUENCES

The cDNA sequence and corresponding deduced amino acid sequence of the described NHK are presented in the Sequence Listing.

Expression analysis has provided evidence that the described NHK can be expressed in a range of human tissues. The described NHK represents a novel MAGUK (SEQ ID NOS: 1–2). Given the physiological importance of protein kinases, they have been subject to intense scrutiny as exemplified and discussed in U.S. Pat. No. 5,817,479, herein incorporated by reference in its entirety, which describes uses and utilities that are applicable to the described NHK.

The described sequences were compiled from sequences available in GENBANK and cDNAs generated from fetal kidney, spleen, and spinal cord mRNAs (Edge Biosystems, Gaithersburg, Md.).

A G/C polymorphism was detected in SEQ ID NO:1 at position 427 which can result in either an asp or his being present at corresponding amino acid position 144 of SEQ ID NO:2.

The gene encoding SEQ ID NO:1–2 is apparently present on human chromosome 2 (see GENBANK accession no. AC067825). Accordingly, the described sequences are also useful for mapping the corresponding coding regions of the human genome.

The described novel human polynucleotide sequences can be used, among other things, in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458 which are herein incorporated by reference in their entirety.

NHK gene products can also be expressed in transgenic animals. Animals of any species including, but not limited to, worms, mice, rats, rabbits, guinea pigs, pigs, micro-pigs, birds, goats, and non-human primates, e.g., baboons, monkeys, and chimpanzees may be used to generate NHK transgenic animals.

Any technique known in the art may be used to introduce a genetically engineered NHK transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus-mediated gene transfer into germ lines (Van der Putten et al., 1985, Proc. Natl. Acad. Sci. USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHK transgene in all their cells, as well as animals which carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell-type by following, for example, the teaching of Lasko et al., 1992, Proc. Natl. Acad. Sci. USA 89:6232–6236. The regulatory sequences required for such a cell-type specific activation will depend upon the particular cell-type of interest, and will be apparent to those of skill in the art.

When it is desired that a NHK transgene be integrated into the chromosomal site of the endogenous NHK gene, gene targeting is preferred. Briefly, when such a technique is to be utilized, vectors containing some nucleotide sequences homologous to the endogenous NHK gene are designed for the purpose of integrating, via homologous recombination with chromosomal sequences, into and disrupting the function of the nucleotide sequence of the endogenous NHK gene (i.e., "knockout" animals).

The transgene can also be selectively introduced into a particular cell-type, thus inactivating the endogenous NHK gene in only that cell-type, by following, for example, the teaching of Gu et al., 1994, Science, 265:103–106. The regulatory sequences required for such a cell-type specific inactivation will depend upon the particular cell-type of interest, and will be apparent to those of skill in the art.

Once transgenic animals have been generated, the expression of the recombinant NHK gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of NHK gene-expressing tissue, may also be evaluated immunocytochemically using antibodies specific for the NHK transgene product.

The present invention also provides for "knock-in" animals. Knock-in animals are those in which a polynucleotide sequence (i.e., a gene or a cDNA) that the animal does not naturally have in its genome is inserted in such a way that the sequence is expressed. Examples include, but are not limited to, a human gene or cDNA used to replace its murine ortholog in the mouse, a murine cDNA used to replace the murine gene in the mouse, and a human gene or cDNA or murine cDNA that is tagged with a reporter construct used to replace the murine ortholog or gene in the mouse. Such replacements can occur at the locus of the murine ortholog or gene, or at another specific site. Such knock-in animals are useful for the in vivo study, testing and validation of, intra alia, human drug targets, as well as for compounds that are directed at the same and therapeutic proteins.

NHK AND NHK POLYPEPTIDES

NHK products, polypeptides, peptide fragments, mutated, truncated, or deleted forms of the NHK, and/or NHK fusion proteins can be prepared for a variety of uses. These uses include, but are not limited to, the generation of antibodies, as reagents in diagnostic assays, the identification of other cellular gene products related to the NHK, as reagents in assays for screening for compounds that can be used as pharmaceutical reagents useful in the therapeutic treatment of mental, biological, or medical disorders and disease.

The Sequence Listing discloses the amino acid sequence encoded by the described NHK-encoding polynucleotides. The NHK displays an initiator methionine that is present in a DNA sequence context consistent with eucaryotic translation initiation sites. SEQ ID NO:2 displays a consensus signal sequence similar to that typically seen in secreted or membrane proteins (the MAGUKs such as the described NHK are typically membrane proteins).

The NHK amino acid sequence of the invention includes the amino acid sequence presented in the Sequence Listing as well as analogues and derivatives thereof. Further, corresponding NHK homologues from other species are encompassed by the invention. In fact, any NHK protein encoded by the NHK nucleotide sequences described above are within the scope of the invention, as are any novel polynucleotide sequences encoding all or any novel portion of an amino acid sequence presented in the Sequence Listing. The degenerate nature of the genetic code is well-known, and, accordingly, each amino acid presented in the Sequence Listing, is generically representative of the well-known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to a NHK encoded by the presently described nucleotide sequences as judged by any of a number of criteria, including, but not limited to, the ability to bind and modify a NHK substrate, or the ability to effect an identical or complementary downstream pathway, or a change in cellular metabolism (e.g., proteolytic activity, ion flux, tyrosine phosphorylation, etc.). Such functionally equivalent NHK proteins include, but are not limited to, additions or substitutions of amino acid residues within the amino acid sequence encoded by the NHK nucleotide sequences described above, but which result in a silent change, thus producing a functionally equivalent expression product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHK nucleotide sequences of the invention. Where the NHK peptide or polypeptide can exist, or has been engineered to exist, as a soluble or secreted molecule, the soluble NHK peptide or polypeptide can be recovered from the culture media. Such expression systems also encompass engineered host cells that express a NHK, or functional equivalent, in situ. Purification or enrichment of a NHK from such expression systems can be accomplished using appropriate detergents and lipid micelles and methods well-known to those skilled in the art. However, such engineered host cells themselves may be used in situations where it is important not only to retain the structural and functional characteristics of the NHK, but to assess biological activity, e.g., in certain drug screening assays.

The expression systems that may be used for purposes of the invention include, but are not limited to, microorganisms such as bacteria (e.g., E. coli, B. subtilis) transformed with recombinant bacteriophage DNA, plasmid DNA or cosmid DNA expression vectors containing NHK nucleotide sequences; yeast (e.g., Saccharomyces, Pichia) transformed with recombinant yeast expression vectors containing NHK nucleotide sequences; insect cell systems infected with recombinant virus expression vectors (e.g., baculovirus) containing NHK nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHK nucleotide sequences; or mammalian cell systems (e.g., COS, CHO, BHK, 293, 3T3) harboring recombinant expression constructs containing NHK nucleotide sequences and promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHK product being expressed. For example, when a large quantity of such a protein is to be produced for the generation of pharmaceutical compositions of or containing NHK, or for raising antibodies to a NHK, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHK coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with gluta-thione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, *Autographa californica* nuclear polyhedrosis virus (AcNPV) is used as a vector to express foreign polynucleotide sequences. The virus grows in *Spodoptera frugiperda* cells. A NHK coding sequence can be cloned individually into non-essential regions (for example the polyhedrin gene) of the virus and placed under control of an AcNPV promoter (for example the polyhedrin promoter). Successful insertion of NHK coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHK nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHK product in infected hosts (e.g., See Logan & Shenk, 1984, Proc. Natl. Acad. Sci. USA 81:3655–3659). Specific initiation signals may also be required for efficient translation of inserted NHK nucleotide sequences. These signals include the ATG initiation codon and adjacent sequences. In cases where an entire NHK gene or cDNA, including its own initiation codon and adjacent sequences, is inserted into the appropriate expression vector, no additional translational control signals may be needed. However, in cases where only a portion of a NHK coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHK sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHK product. Such engineered cell lines may be particularly useful in screening and evaluation of compounds that affect the endogenous activity of the NHK product.

A number of selection systems can be used including, but not limited to, the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Proc. Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

Also encompassed by the present invention are fusion proteins that direct the NHK to a target organ and/or facilitate transport across the membrane into the cytosol. Conjugation of a NHK product to antibody molecules or their Fab fragments could be used to target cells bearing a particular epitope. Attaching the appropriate signal sequence to the NHK would also transport the NHK to the desired location within the cell. Alternatively targeting of NHK or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHK to the target site or desired organ, where they cross the cell membrane and/or the nucleus where the NHK can exert its functional activity. This goal may be achieved by coupling of the NHK to a cytokine or other ligand that provides targeting specificity, and/or to a protein transducing domain (see generally U.S. application Ser. Nos. 60/111,701 and No. 60/056,713, both of which are herein incorporated by reference, for examples of such transducing sequences) to facilitate passage across cellular membranes and can optionally be engineered to include nuclear localization.

ANTIBODIES TO NHK PRODUCTS

Antibodies that specifically recognize one or more epitopes of a NHK, or epitopes of conserved variants of a NHK, or peptide fragments of a NHK are also encompassed by the invention. Such antibodies include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention can be used, for example, in the detection of NHK in a biological sample and may, therefore, be utilized as part of a diagnostic or prognostic technique whereby patients may be tested for abnormal amounts of NHK. Such antibodies may also be utilized in conjunction with, for example, compound screening schemes for the evaluation of the effect of test compounds on expression and/or activity of a NHK expression product. Additionally, such antibodies can be used in conjunction gene therapy to, for example, evaluate the normal and/or engineered NHK-expressing cells prior to their introduction into the patient. Such antibodies may additionally be used as a method for the inhibition of abnormal NHK activity. Thus, such antibodies may, therefore, be utilized as part of treatment methods.

For the production of antibodies, various host animals may be immunized by injection with the NHK, a NHK peptide (e.g., one corresponding to a functional domain of a NHK), truncated NHK polypeptides (NHK in which one or more domains have been deleted), functional equivalents of the NHK or mutated variant of the NHK. Such host animals may include, but are not limited to, pigs, rabbits, mice, goats, and rats, to name but a few. Various adjuvants may be used to increase the immunological response, depending on the host species including, but not limited to, Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci. USA 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150,584 and respective disclosures which are herein incorporated by reference in their entirety.

Alternatively, techniques described for the production of single chain antibodies (U.S. Pat. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHK expression products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHK can, in turn, be utilized to generate anti-idiotype antibodies that "mimic" a given NHK, using techniques well-known to those skilled in the art. (See, e.g., Greenspan & Bona, 1993, FASEB J. 7(5):437–444; and Nissinoff, 1991, J. Immunol. 147(8):2429–2438). For example antibodies which bind to a NHK domain and competitively inhibit the binding of NHK to its cognate receptor/ligand can be used to generate anti-idiotypes that "mimic" the NHK and, therefore, bind, activate, or neutralize a NHK, NHK receptor, or NHK ligand. Such anti-idiotypic antibodies or Fab fragments of such anti-idiotypes can be used in therapeutic regimens involving a NHK-mediated pathway.

Additionally given the high degree of relatedness of mammalian NHKs, the presently described knock-out mice (having never seen NHK, and thus never been tolerized to NHK) have a unique utility, as they can be advantageously applied to the generation of antibodies against the disclosed mammalian NHK (i.e., NHK will be immunogenic in NHK knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a nucleotide sequence that is described in SEQ ID NO:1.

2. An isolated nucleic acid molecule comprising a nucleotide sequence encoding the amino acid sequence shown in SEQ ID NO:2.

3. An isolated nucleic acid molecule comprising a nucleotide sequence that:

(a) encodes the amino acid sequence shown in SEQ ID NO:2; and (b) hybridizes under stringent conditions to the nucleotide sequence of SEQ ID NO:1 or the complement thereof.

* * * * *